United States Patent [19]

Schneider

[11] Patent Number: 4,743,233

[45] Date of Patent: May 10, 1988

[54] SAFETY CAP SYRINGE

[75] Inventor: Michael B. Schneider, Springfield, Ill.

[73] Assignee: Schneider Medical Technologies, Inc., Chicago, Ill.

[21] Appl. No.: 942,811

[22] Filed: Dec. 22, 1986

Related U.S. Application Data

[63] Continuation of Ser. No. 824,259, Jan. 23, 1986, abandoned.

[51] Int. Cl.$^4$ ............................................. A61M 5/32
[52] U.S. Cl. ..................................... 604/192; 604/198
[58] Field of Search ................ 604/192, 197, 198, 263

[56] References Cited

U.S. PATENT DOCUMENTS 2,408,323  6/1943  Lockhart .
4,425,120  1/1984  Sampson et al. ..................... 604/263
4,631,057  12/1986  Mitchell ............................... 604/198
4,655,751  4/1987  Harbaugh .

Primary Examiner—John D. Yasko
Attorney, Agent, or Firm—Hill, Van Santen, Steadman & Simpson

[57] ABSTRACT

A safety syringe has a slidable sleeve over the syringe barrel that is connectable in a first position extending over the hypodermic needle and that is reconnectable in a second position along the syringe barrel to expose the needle for use.

15 Claims, 1 Drawing Sheet

U.S. Patent
May 10, 1988
4,743,233
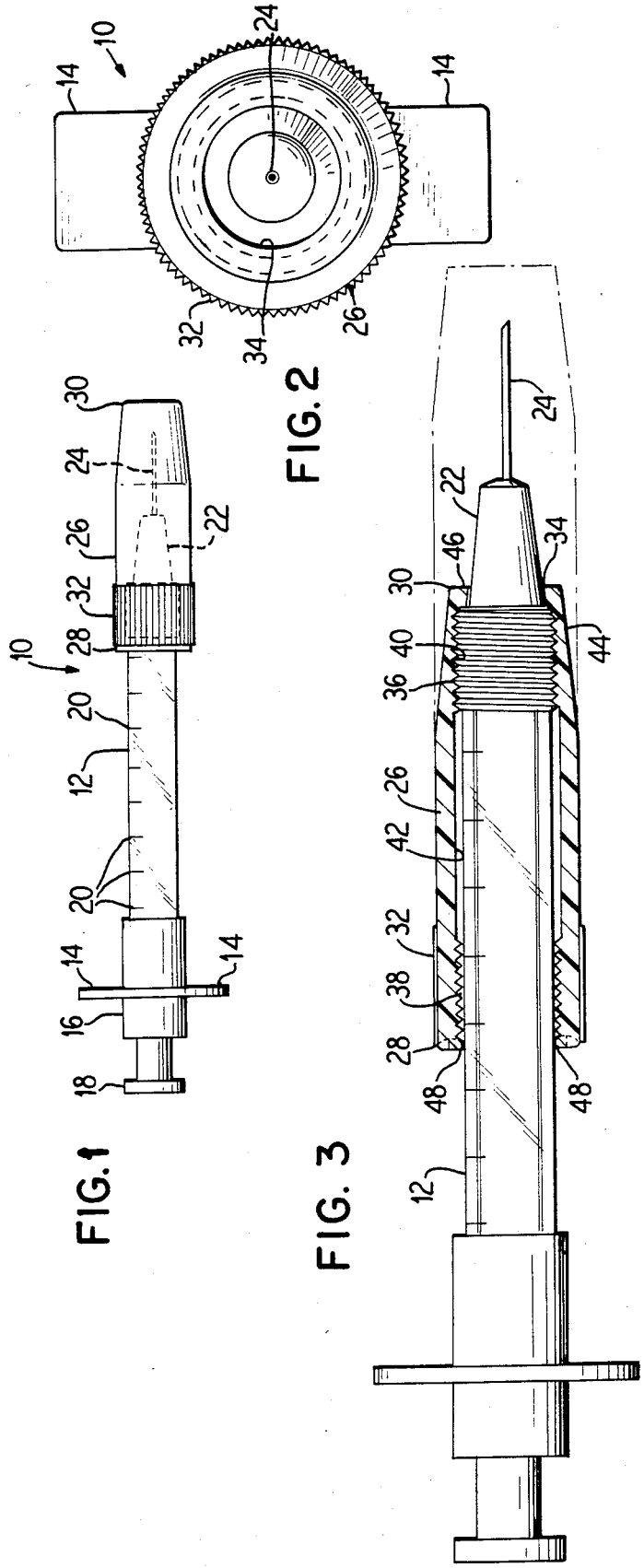
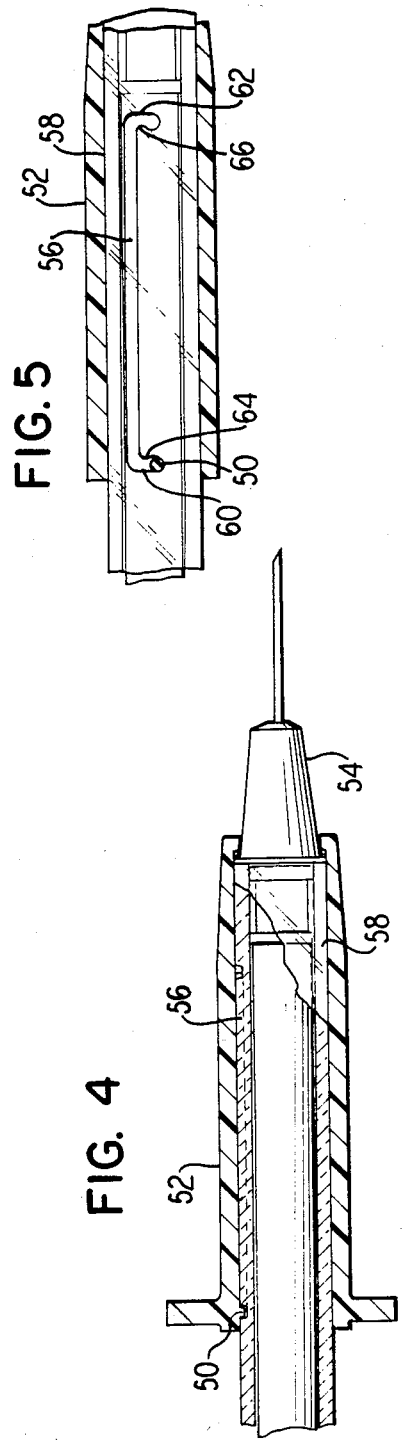

SAFETY CAP SYRINGE

This is a continuation of application Ser. No. 824,259 filed Jan. 23, 1986, now abandoned.

BACKGROUND OF THE INVENTION

1. Field of the Invention

The present invention relates to a safety cap for use on a hypodermic syringe.

2. Description of the Prior Art

Hypodermic needles on syringes are generally provided with a protective cap which is removed from the syringe prior to an injection and which is frequently replaced after the hypodermic needle is used, both to prevent injury from exposed needles and out of habit. In recapping the hypodermic needle, the exposed needle and cap are moved toward one another with the cap held in the hand. This can result in missing the cap and piercing of the skin by the used needle, particularly for health care workers giving frequent injections. Such accidental "sticks" most frequently occur during recapping and pose a serious health hazard to health care workers treating patients with infectious diseases, such as hepatitis or AIDS, since the used needle is generally contaminated with the disease-causing virus or bacteria.

SUMMARY OF THE INVENTION

The present invention significantly reduces the risk of accidental contact with a hypodermic needle, particularly by health care workers attempting to recap a used needle and, thus, reduces the risk of contracting infectious diseases during treatment of patients. The present invention is embodied in a safety syringe having a generally cylindrical safety sleeve over the hypodermic needle which is slidably movable along the syringe barrel to expose the hypodermic needle for use. After use, the safety sleeve is replaced over the needle by sliding the sleeve forward along the syringe barrel without risk of the health care worker coming in contact with the contaminated needle.

The safety sleeve can be locked into position in either the open or closed position, and at least a portion of the sleeve is transparent to enable volume markings on the syringe to be visible during use. The present invention can be utilized on syringes of various sizes and types, it is inexpensive to manufacture and simple to use, yet significantly reduces health risks to health care workers.

BRIEF DESCRIPTION OF THE DRAWINGS

FIG. 1 is an elevational view of a medicinal syringe incorporating a safety sleeve according to the principles of the present invention;

FIG. 2 is an end elevational view of the syringe shown in FIG. 1, taken from the right;

FIG. 3 is an enlarged elevational view, partially in cross section of the syringe of FIG. 1, showing the safety sleeve in an open position;

FIG. 4 is a partial cross section of a second embodiment of a safety syringe according to the principles of the present invention; and FIG. 5 is a fragmentary plan view of the device of FIG. 4 showing a locking track mechanism.

DESCRIPTION OF THE PREFERRED EMBODIMENTS

In FIG. 1, a safety syringe according to the present invention is shown generally at 10, including a cylindrical syringe barrel 12 having a pair of finger tabs 14 projecting transversely therefrom at a first end 16 and a plunger 18 extending into the hollow interior of the barrel 12 for sliding movement therealong, the position of the plunger 16 being indicated by spaced markings or graduations 20 at an exterior surface of the barrel 12. From an opposite barrel end 22 extends a hypodermic needle 24 in fluid communication with the interior of the barrel 12. A safety sleeve 26 is mounted adjacent the barrel end 22 and extends axially to shroud the needle 24. The safety sleeve 26, when in a closed needle protecting position as shown in FIG. 1, has a first end 28 secured to the barrel 12 while a second end 30 extends beyond the end of the hypodermic needle 18 to protect those working with the syringe 10 from contact with the needle 18. The sleeve 26 in one embodiment, has splines 32 adjacent the end 28 of the safety sleeve 26.

Referring to FIG. 2, the sleeve 26 has a generally cylindrical shape with an opening 34 at the end 30 through which the needle 24 extends when the safety sleeve is moved to an open, needle exposed position.

In an embodiment shown in FIG. 3, the barrel 12 includes a threaded portion 36 adjacent the end 22. A pair of like threaded portions 38 and 40 are formed at an internal surface 42 of the sleeve 26 adjacent the respective sleeve ends 28 and 30. When the protective sleeve 26 is in the closed position, as shown in FIG. 1 or in dotted outline in FIG. 3, the threaded portion 38 is threaded over the barrel threads 36 so that the protective sleeve 26 is securely affixed to the syringe 10 and thereby protects health care workers from contact with needle 18. By rotating the sleeve 26, such as by gripping the splined portion 32, the threaded portion 38 is disengaged from the barrel threads 36 and the sleeve 26 is thereafter slidably moved along the barrel 12 toward the tabs 14 to expose the needle 24. The sleeve 26 is then rotated to threadably engage the threaded portion 40 on the barrel threads 36 and thereby secure the protective sleeve 26 in an open position so that the syringe 10 is ready for use.

The sleeve end 30 is tapered at 44 to enable injections to be given at an acute angle. The sleeve 26 is also somewhat shorter than the barrel 12, in the preferred embodiment, to provide unrestricted access to the finger tabs 14. The sleeve 26, thus, provides minimal interference with the use of the syringe 10.

Once used, the sleeve 26 is gripped by the splines 32 and turned in a reverse direction until the portion 40 disengages the barrel threads 36. The sleeve 26 is slid forward and again turned until the portion 38 engages the barrel threads 36, ensuring that the sleeve 26 is securely in place to shield the needle 24. Thus, in the present device, the user's hands do not come near the hypodermic needle 24 during recapping.

The movement of the sleeve 26 beyond the respective open and closed positions is restricted. For instance, at the end 30, an annular flange 46 extends inwardly of the opening 34 to prevent the sleeve 26 from being moved beyond a predetermined open position. Similarly, spaced tabs 48 are provided at the sleeve end 28 to restrict movement of the sleeve 26 beyond a predetermined closed position. In one embodiment, the tabs 48 are directed inwardly at diametrically opposed positions on the end 28 and are sufficiently flexible to enable the sleeve 26 to be initially threaded over the barrel threads 36 during assembly of the present device 10, yet inhibit the complete removal of the sleeve 26 from the syringe 10.

It is within the spirit of the present invention to utilize a variety of locking and fastening mechanisms between the syringe 10 and the safety sleeve 26. For instance, in FIG. 4, a projection 50 extends inwardly from a safety sleeve 52 mounted on a syringe 54. The projection 50 rides in a slot or channel 56 formed in a barrel 58 of the syringe 54. As seen more clearly in FIG. 5, the slot 56 extends longitudinally of the barrel 58 and includes locking positions 60 and 62 at the respective slot ends. Small projections 64 and 66 restrict somewhat the width of the slot 56 adjacent the locking portion 60 and 62, respectively, so that as the projection 50 is moved into the locking positions 60 and 62, it is held therein by the restricting projections 64 and 66. The embodiment shown in FIGS. 4 and 5, thus, enables the protecting sleeve 52 to be quickly released from either its open or closed position simply by rotating the sleeve 52 slightly and then by sliding the sleeve 52 so that the projection 50 remains in the slot 56, and repositioning the sleeve 52 at the alternate position. Alternatively, a projection could extend from the syringe barrel into a slot or channel in the safety sleeve.

The protective sleeve is to have at least a portion thereof formed of transparent material so that volume marks on the syringe cylinder are visible while the device is in use. The embodiment in FIGS. 4 and 5 enables the volume marks on the syringe barrel to be visible throughout the length of the sleeve since no threaded portions are required for locking the protective sleeve in position.

The present invention, thus, provides a safety syringe which may be used by health care workers in treating infectious diseases with a decreased risk of self-infection due to contact with the contaminated needle. The safety sleeve is securable in a closed position over the needle so that once the syringe is used, it may be laid aside or disposed of without the possiblity of accidental puncture of the skin by the hypodermic needle. The sliding sleeve is repositionable between an open position and a closed position with little risk of accidental contact with the needle.

As is apparent from the foregoing specification, the invention is susceptible to being embodied with various alterations and modifications which may differ particularly from those that I have described in the preceding specification and description. It should be understood that I wish to embody within the scope of the patent granted hereon all such modifications as reasonably and properly, within my contribution to the art.

I claim as my invention:

1. A hypodermic syringe for giving injections, comprising:
   a hollow barrel having first and second opposite ends;
   a plunger slidably movable within said barrel and extending from said first barrel end;
   a hypodermic needle mounted extending axially outward from said second opposite end of said barrel and said barrel;
   a sleeve encircling a portion of said barrel and slidably movable between a first position being characterized by said needle projecting from said sleeve and a second position being characterized by said needle being contained within said sleeve; and
   a first rotationally locking engaging means for engagement between said sleeve and said barrel and selectively rotationally fastenable to securely maintain said sleeve in said second position, said first engaging means preventing accidental movement of said sleeve from said second position;
   an end of said sleeve extending in the direction of said hypodermic needle being tapered inwardly to provide clearance during use of said syringe when said sleeve is in said first position;
   whereby accidental contact with said needle is prevented by said sleeve when in said second position.

2. A syringe as claimed in claim 1, wherein at least a portion of said sleeve is transparent and said barrel includes volume markings.

3. A hypodermic syringe for giving injections, comprising:
   a hollow barrel having first and second opposite ends;
   a plunger slidably movable within said barrel and extending from said first barrel end;
   a hypodermic needle mounted extending axially outward from said second opposite end of said barrel and being in fluid communication with an interior of said barrel;
   a sleeve encircling a portion of said barrel and slidably movable between a first position being characterized by said needle projecting from said sleeve and a second position being characterized by said needle being contained within said sleeve; and
   a first engaging means for engaging between said sleeve and said barrel and selectively fastenable to securely maintain said sleeve in said second position, said first engaging means preventing accidental movement of said sleeve from said second position, said engaging means includes a threaded barrel portion on said barrel adjacent said second opposite end, and first and second threaded sleeve portions adjacent respective opposite ends of said sleeve from alternately threadably engaging said threaded barrel portion and thereby securing said sleeve in said respective first and second positions;
   whereby accidental contact with said needle is prevented by said sleeve when in said second position.

4. A hypodermic syringe for giving injections, comprising:
   a hollow barrel having first and second opposite ends;
   a plunger slidably movable within said barrel and extending from said first barrel end;
   a hypodermic needle mounted extending axially outward from said second opposite end of said barrel and being in fluid communication with an interior of by said needle projecting from said sleeve and a second position being characterized by said needle being contained within said sleeve; and
   a first rotationally locking engaging means for engagement between said sleeve and said barrel and selectively rotationally fastenable to securely maintain said sleeve in said second position, said first engaging means preventing accidental movement of said sleeve from said second position, said engaging means including a longitudinal channel formed in an exterior surface of said barrel, and a projection extending inwardly on an interior of said sleeve for movement along said channel;
   whereby accidental contact with said needle is prevented by said sleeve when in said second position.

5. A hypodermic syringe for giving injections, comprising:

a hollow barrel having first and second opposite ends;

a plunger slidably movable within said barrel and extending from said first barrel end;

a hypodermic needle mounted extending axially outward from said second opposite end of said barrel and being in fluid communication with an interior of said barrel;

a sleeve encircling a portion of said barrel and slidably movable between a first position being characterized being in fluid communication with an interior of said barrel;

a sleeve encircling a portion of said barrel and slidably movable between a first position being characterized by said needle projecting from said sleeve and a second position being characterized by said needle being contained within said sleeve; and a first rotationally locking engaging means for engagement between said sleeve and said barrel and selectively rotationally fastenable to securely maintain said sleeve in said second position, said first engaging means preventing accidental movement of said sleeve from said second position, said first rotationally locking engaging means including a longitudinally extending channel having transversely extending locking portions at opposite channel ends, and a projection extending into said channel and moving along said channel during sliding movement of said sleeve;

whereby accidental contact with said needle is prevented by said sleeve when in said second position.

6. A syring as claimed in claim 5, wherein said channel includes a circumferentially extending locking means at first and second opposite ends.

7. A hypodermic syringe as claimed in claim 1, wherein said longitudinally extending channel is formed in an interior of said sleeve and said projection extends from an exterior surface of said barrel for movement along said channel.

8. A hypodermic syringe for giving injections, comprising:

a hollow barrel having first and second opposite ends;

a plunger slidably movable within said barrel and extending from said first barrel end;

a hypodermic needle mounted extending axially outward from said second opposite end of said barrel and being in fluid communication with an interior of said barrel;

a sleeve encircling a portion of said barrel and slidably movable between a first position being characterized by said needle projecting from said sleeve and a second position being characterized by said needle being contained within said sleeve; and a first rotationally locking engaging means for engagement between the said sleeve and said barrel and selectively rotationally fastenable to securely maintain said sleeve in said second position, said first engaging means preventing accidental movement of said sleeve from said second position, said engaging means including a longitudinal channel formed in an interior of said sleeve and a projection extending from an exterior surface of said barrel for movement along said channel, and said channel including circumferentially extending locking means at first and second opposite ends;

whereby accidental contact with said needle is prevented by said sleeve when in said second position.

9. A syringe as claimed in claim 1, wherein said barrel includes first and second finger tabs projecting transversely from said first barrel end and said sleeve is spaced from said finger tabs when said sleeve is in said first position.

10. A safety cap for use on a syringe having a cylindrical barrel and a hypodermic needle extending from a first end of said barrel, comprising:

a substantially cylindrical member having first and second opposite ends and mounted over said first barrel end, at least a portion of said cylindrical member being formed of transparent material;

a first rotationally locking fastening means for selectively securing said first opposite end of said cylindrical member adjacent said first barrel end, said first rotationally locking fastening means including a projection extending from said barrel for selective engagement into a first restricted locking portion adjacent said first end of said cylindrical member;

a second rotationally locking fastening means spaced from said first fastening means for selectively rotatably securing said second opposite end of said cylindrical member to said first barrel end, said cylindrical member extending around said needle when said second engaging means is rotatably secured, at least said second rotatably locking fastening means preventing accidental disengagement of said second fastening means, said second rotationally locking fastening means including a second restricted locking portion adjacent said second end of said cylindrical member for selective engagement with said projection extending from said barrel; and said cylindrical member being freely slidable along the syringe barrel when said first and second rotationally locking fastening means are disengaged;

said cylindrical member is alternately securable by said first fastening means and by said second fastening means.

11. An improved syringe having a piston manually slidable along an interior of a cylindrical body and a hypodermic needle mounted extending axially from a first end of said cylindrical body, the improvement comprising:

a substantially transparent cap having first and second open ends and being slidably received over said cylindrical body;

means for alternately locking said cap in first and second positions to said cylindrical body, said first position characterized by said cap enshrouding said needle and said second position characterized by said cap being clear of said needle, said locking means including a first threaded portion at an inside surface of said first open end and a second threaded portion at an inside surface of said second open end and a third threaded portion on an outside surface of said cylindrical body of said syringe for alternate cooperative engagement with said first and second threaded portions; and said substantially transparent cap having a generally smooth obstruction-free inside surface extending between said first and second threaded portions for sliding movement of said cap along said cylindrical body between said first and second positions; said cap having at least a portion of the outside surface forming a transparent window for viewing markings on said cylindrical body.

12. A hypodermic syringe for giving injections, comprising:

a hollow barrel having first and second opposite ends;

a plunger slidably movable within said barrel and extending from said first barrel end;

a hypodermic needle mounted extending axially outward from said second opposite end of said barrel and being in fluid communication with an interior of said barrel;

a sleeve encircling a portion of said barrel and slidably movable between a first position being characterized by said needle projecting from said sleeve and a second position being characterized by said needle being contained within said sleeve;

a first engaging means for engagement between said sleeve and said barrel and selectively fastenable to securely maintain said sleeve in said second position, said first engaging means presenting accidental movement of said sleeve from said second position;

said sleeve including an inwardly projecting annular flange for abutting said second barrel end to restrict movement of said sleeve beyond said first position; and said first engaging means including a threaded connection between said sleeve and said barrel;

whereby accidental contact with said needle is prevented by said sleeve when in said second position.

13. A hypodermic syringe for giving injections, comprising:

a hollow barrel having first and second opposite ends;

a plunger slidably movable within said barrel and extending from said first barrel end;

a hypodermic needle mounted extending axially outward from said second opposite end of said barrel and being in fluid communication with an interior of said barrel;

a sleeve encircling a portion of said barrel and slidably movable between a first position being characterized by said needle projecting from said sleeve and a second position being characterized by said needle being contained within said sleeve;

a first engaging means for engagement between said sleeve and said barrel and selectively fastenable to securely maintain said sleeve in said second position, said first engaging means preventing accidental movement of said sleeve from said second position;

said sleeve including an inwardly projecting annular flange for abutting said second barrel end to restrict movement of said sleeve beyond said first position; and said first engaging means including a longitudinally extending channel having transversely extending locking portions at opposite channel ends, and a projection extending into said channel and moving along said channel during sliding movement of said sleeve;

whereby accidental contact with said needle is prevented by said sleeve when in said second position.

14. An improved syringe having a piston manually slidable along an interior of a cylindrical body and a hypodermic needle mounted extending axially from a first end of said cylindrical body, the improvement comprising:

a substantially transparent cap having first and second open ends and being slidably received over said cylindrical body;

means for alternately locking said cap in first and second positions to said cylindrical body, said first position characterized by said cap enshrouding said needle and said second position characterized by said cap being clear of said needle, said locking means including a first circumferentially extending portion at an inside surface of said first open end and a second circumferentially extending portion at an inside surface of said second open end and a third mating portion on an outside surface of said cylindrical body of said syringe for alternate cooperative engagement with said first and second circumferentially extending portions; and said substantially transparent cap having a generally smooth obstruction-free inside surface extending between said first and second circumferentially extending portions for sliding movement of said cap along said cylindrical body between said first and second positions; said cap having at least a portion of the outside surface forming a transparent window for viewing markings on said cylindrical body.

15. A hypodermic syringe for giving injections, comprising:

a hollow barrel having first and second opposite ends;

a plunger slidably movable within said barrel and extending from said first barrel end;

a hypodermic needle mounted extending axially outward from said second opposite end of said barrel and being in fluid communication with an interior of said barrel;

a sleeve encircling a portion of said barrel and slidably movable between a first position being characterized by said needle projecting from said sleeve and a second position being characterized by said needle being contained within said sleeve; and a first engagement means for engagement between said sleeve and said barrel and selectively fastenable to securely maintain said sleeve in said second position, said first engaging means preventing accidental movement of said sleeve from said second position, said first engaging means including a threaded barrel portion of said barrel adjacent said second opposite end, and a threaded sleeve portion adjacent an end of said sleeve for threadably engaging said threaded barrel portion and thereby securing said sleeve in said second position;

whereby accidental contact with said needle is prevented by said sleeve when in said second position.

* * * * *